United States Patent [19]
Rodak et al.

[11] Patent Number: 5,352,237
[45] Date of Patent: Oct. 4, 1994

[54] ENDOSCOPIC INSTRUMENT INCLUDING A HANDLE HAVING A FLYWHEEL MECHANISM

[75] Inventors: Daniel P. Rodak, Milford; Paul A. Matula, Brookfield, both of Conn.

[73] Assignee: United States Surgical Corporation, Norwalk, Conn.

[21] Appl. No.: 14,805

[22] Filed: Feb. 8, 1993

[51] Int. Cl.⁵ ............................................. A61B 17/28
[52] U.S. Cl. .................... 606/206; 606/205; 128/751; 128/20; 604/159
[58] Field of Search ............... 606/205, 206, 170, 171, 606/140, 141, 174; 128/20, 751, 4; 604/159; 602/26

[56] References Cited

U.S. PATENT DOCUMENTS

| | | | |
|---|---|---|---|
| 3,826,256 | 7/1974 | Smith | 604/159 |
| 4,342,313 | 8/1982 | Chittenden | 604/159 |
| 4,483,326 | 11/1984 | Yamaka et al. | 128/4 |
| 4,503,842 | 3/1985 | Takayama | 128/4 |
| 4,643,190 | 2/1987 | Heimberger | |
| 4,733,671 | 3/1988 | Mehl | 606/171 X |
| 4,923,461 | 8/1990 | Caspari et al. | |
| 4,957,498 | 9/1990 | Caspari et al. | |
| 5,009,223 | 4/1991 | DeFonce | 602/26 X |
| 5,195,506 | 3/1993 | Hulfish | 128/20 |

FOREIGN PATENT DOCUMENTS 78017 10/1982 European Pat. Off. ............... 128/4

*Primary Examiner*—Richard J. Apley
*Assistant Examiner*—Beverly A. Meindl

[57] ABSTRACT

A handle for an endoscopic or laparoscopic surgical instrument including a flexible member positioned within a tubular body member extending from the handle. The flexible member is secured about a rotatable flywheel spool in said handle and extends to a tool mechanism at a distal end of the instrument. The flexible member is wound about the flywheel spool and is extended or withdrawn upon movement of the handle.

21 Claims, 4 Drawing Sheets

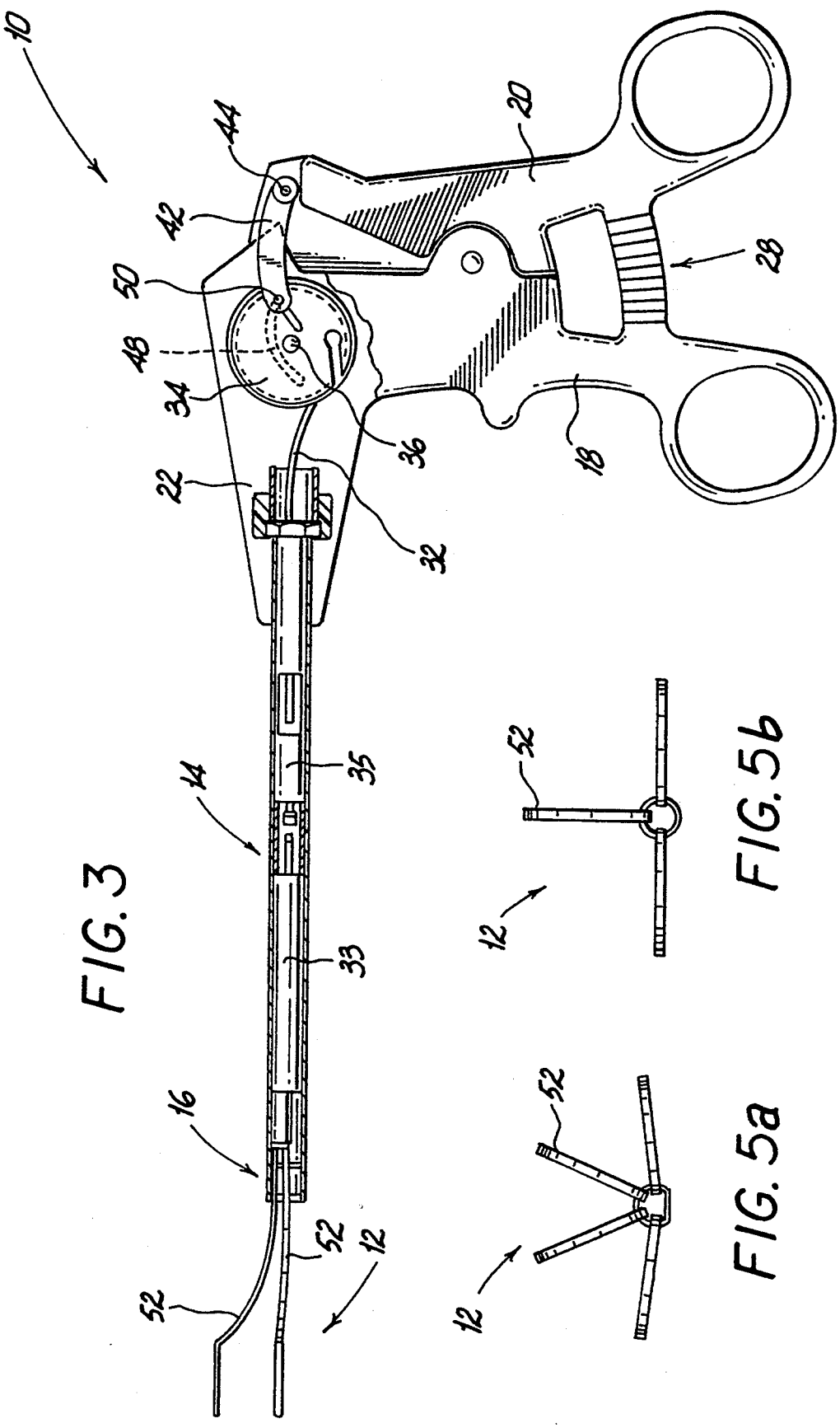

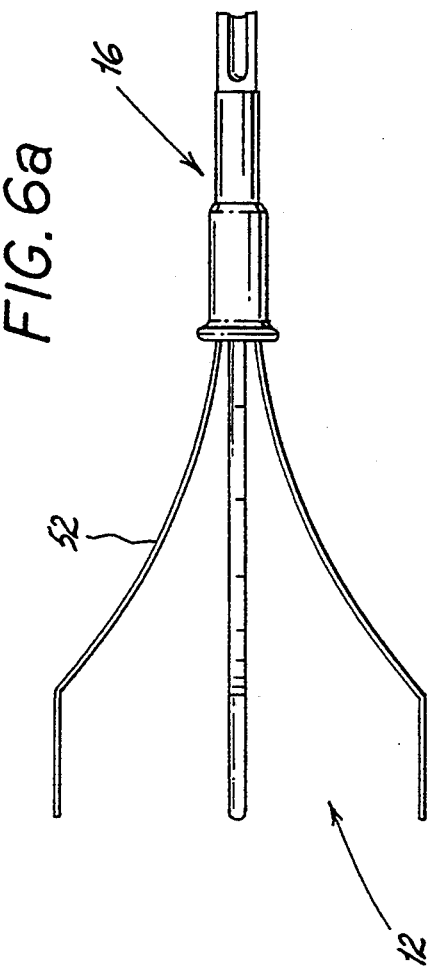
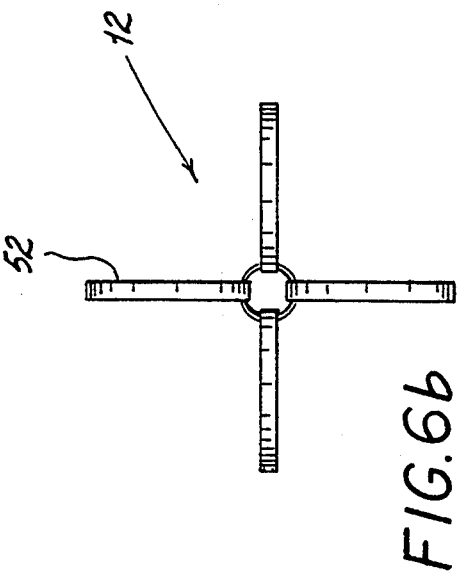
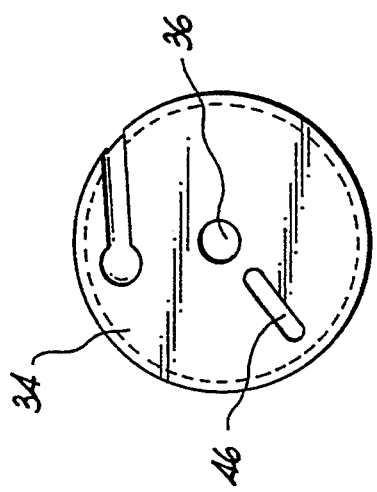

ENDOSCOPIC INSTRUMENT INCLUDING A HANDLE HAVING A FLYWHEEL MECHANISM

BACKGROUND OF THE INVENTION

1. Field of the Invention

The present invention relates to the field of laparoscopic or endoscopic instrumentation and surgery, and more particularly to a handle mechanism of an instrument for manipulating a surgical tool carried on the instrument.

2. Discussion of the Prior Art

A surgeon, when performing an operation on a patient, is often obstructed in his efforts to excise diseased or damaged tissues and organs by surrounding tissues or other organs. Retractor mechanisms have typically been utilized during surgery to retract and retain organs and tissues to clear the surgical site to allow access for the surgeon. In the past, it has generally been the case, when performing gastro intestinal surgery, i.e. surgery within the abdominal cavity, to make a large cut in the abdomen wall to produce a suitable opening to allow access to the interior organs. This cut was generally large enough to allow the use of human hands, either those of the surgeon or those of a member of the surgical team, as a retractor. Surgical personnel would thus be required to insert their hands or a retractor tool member through the incision into the abdominal cavity to push and hold organs and obstructing tissue away from the surgical objective.

Recently, as a result of developments in endoscopic and laparoscopic surgery, instruments have become smaller and are constructed with greater precision. In these procedures, small incisions are made through the surface of the skin in the vicinity of the surgical objective by trocar assemblies which provide a path to the surgical site. Through these incisions, miniaturized surgical instruments such as scissors, forceps, clamps, retractors, video equipment and scalpels may be inserted to perform various surgical procedures. The retractors provide a means for pushing tissue and organs which obstruct the surgical objective, to allow the surgeon access to surgical site.

While endoscopic instruments such as retractors are known in the art, many are operable only between a fully deployed position and a fully retracted position. Those that do provide for controlled opening do so with handle mechanisms which are difficult to operate and require greater dexterity on the part of the surgeon, than the use of other instruments.

Accordingly, a need exists for an endoscopic or laparoscopic retractor mechanism which allows for controlled opening and closing of the blades of the retractor, while the operation of the device is smooth and easy to manipulate. The present invention provides such a device.

SUMMARY OF THE INVENTION

The present invention provides a novel endoscopic instrument having a handle which is useful to manipulate an endoscopic surgical tool positioned distally at the end of the device so that the tool may perform a function within the body. In order to manipulate the tool, the invention provides a handle having a flywheel spool upon which is wound an elongated flexible member. The flywheel spool is rotated upon opening and closing of the handle to manipulate the distal endoscopic surgical tool.

The wound flexible member is secured to the flywheel spool which rotates together with the wound flexible member inside the body of the handle. The flywheel and handle mechanism are joined to each other by a link member through the provision of a pin which is connected to the movable handle of the handle mechanism. The pin is engaged in a slot in the flywheel in a somewhat floating manner to allow for deflection of the flexible member from the longitudinal axis of the handle during movement. The pin is also secured in an arcuate slot in the interior of the handle body which is integrally constructed with the handle body and which defines the path of travel of the pin. The motion of the handles toward and away from each other causes the pin member to move along the arcuate slot defined by the handle body while the pin member also traverses the radially extending slot, thus causing the flexible member to unwind and rewind about the flywheel.

The handle mechanism may also include a pair of arcuate ratcheting arms which extend between the handles and overlap so that the handles may be incrementally moved toward and away from each other, and retained incrementally in intermediate positions.

The instrument itself includes the handle mechanism and an elongated tubular body member which extends from the handle and carries the endoscopic tool adjacent its distal end portion in a retracted position. The elongated flexible member is reciprocatingly positioned in the tubular body member and operatively connected to the tool at the distal end. In use, the distal endoscopic tool and a portion of the tubular body member may be inserted through a cannula of a trocar assembly positioned in a small incision in the body. Once positioned within the body, the tool may be manipulated between its retracted position and a deployed position outside the distal end portion of the tubular member to perform functions within the body. Preferably, the tool mechanism is a retractor mechanism, although any tool may be used.

One embodiment of the instrument includes a retractor device suitable for displacing tissue and organs within the abdominal cavity of the body. The retractor mechanism includes a plurality of elongated finger members which are retained in a retracted position within the distal end portion of the tubular body member. The finger members are movable longitudinally between their retracted position and a deployed position outside the distal end portion of the tubular body member.

As the handles are moved toward each other, the flywheel spool rotates and the wound elongated flexible member begins to unwind and advance the finger members longitudinally from their retracted position to the deployed position. Preferably, the finger members open into a fanned-out pattern, pushing and holding internal organs and tissues aside from the surgical objective, with the ratcheting arms retaining the handles in position. After the surgical objective has been completed, the handles may be moved apart, thus rotating the flywheel spool in the opposite direction and allowing the elongated flexible member to rewind and withdraw the finger members longitudinally to their retracted position, so that the tubular body member and the retracted finger members may be removed from the abdominal cavity. The finger members preferably are constructed of a spring-like material, such as a shape-memory material.

BRIEF DESCRIPTION OF THE DRAWINGS

The foregoing features of the present invention will become more readily apparent and may be understood by referring to the following detailed description of an illustrative embodiment of the instrument according to the present invention, taken in conjunction with the accompanying drawings, in which:

FIG. 3 illustrates a cut-away side view of the embodiment of FIG. 2 with the endoscopic tool shown moved longitudinally to a deployed position in which the tool projects from the distal end of the instrument;

FIGS. 4a and 4b illustrate a side elevational view and a front elevational view, respectively, of the flywheel mechanism of the handle of the instrument of the present invention;

FIGS. 5a and 5b illustrate front end views of endoscopic retractor tools of FIG. 2 in a deployed position; and FIGS. 6a and 6b illustrate a side elevational view and a front end view, respectively, of another embodiment of an endoscopic retractor tool according to the present invention.

DETAILED DESCRIPTION OF THE PREFERRED EMBODIMENTS

Figure 1:
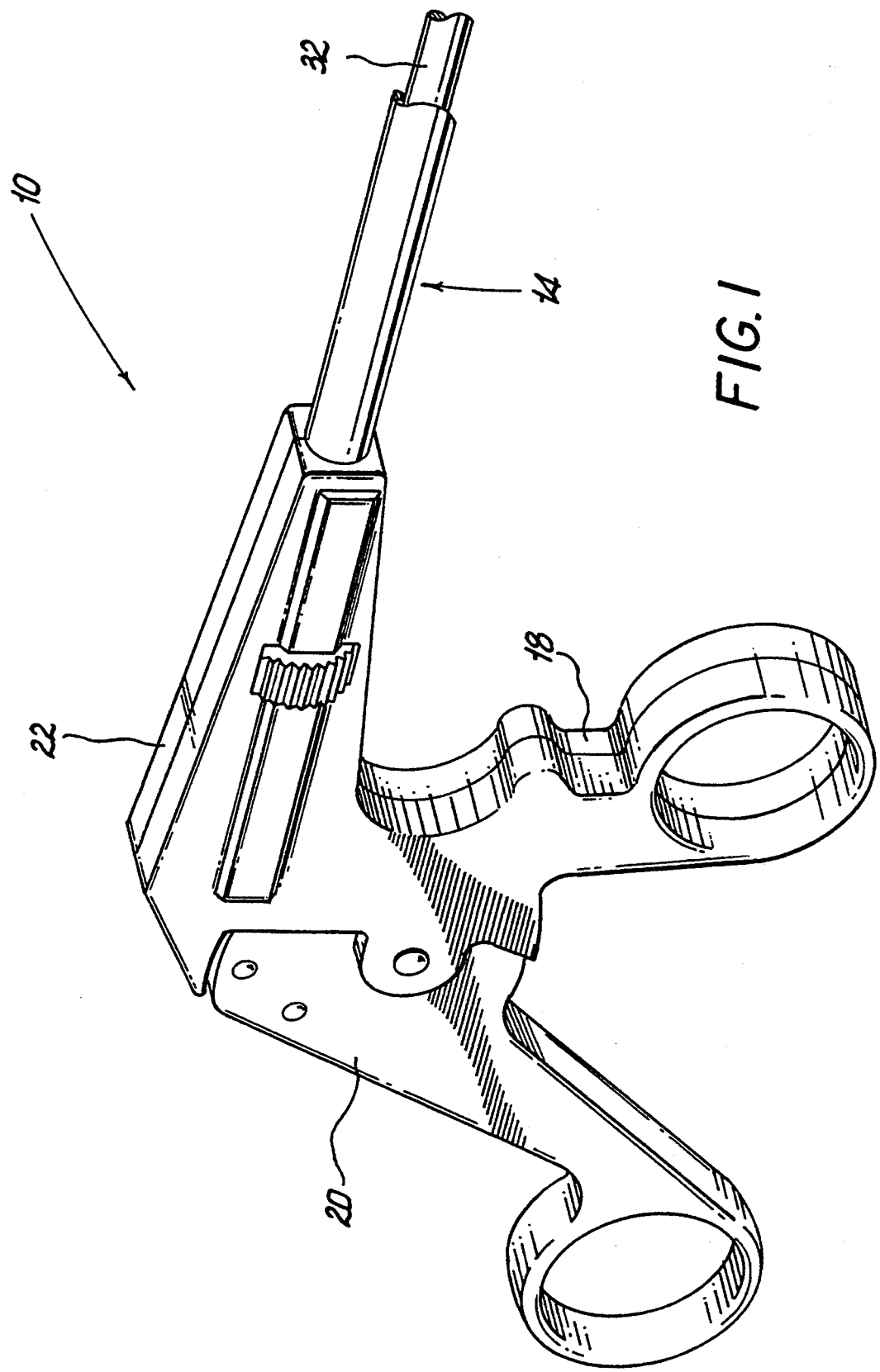
FIG. 1 illustrates a perspective view of an endoscopic instrument employing the handle of the present invention.
Figure 2:
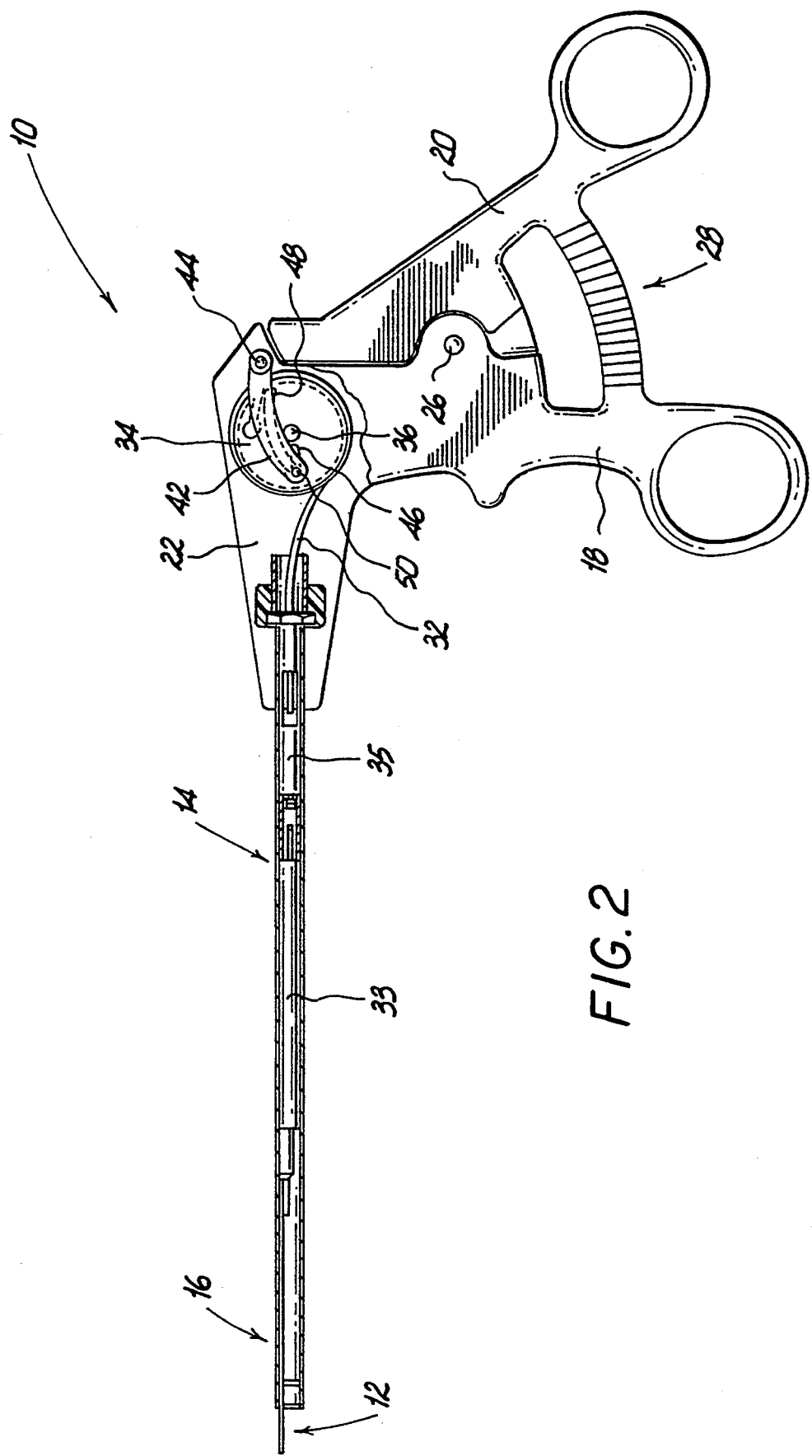
FIG. 2 illustrates a cut-away side view of an embodiment of the instrument in which the endoscopic tool is in a first, retracted position.

Referring to FIG. 1, the handle 10 of the instrument of the present invention is shown, and includes an elongated tubular body member 14. Referring to FIG. 2, body member 14 carries endoscopic tool 12 extending from its distal end portion 16 in a first retracted or covered position. In this manner, the distal endoscopic tool 12 and a portion of tubular body member 14 may be inserted through a cannula into the body. Positioned adjacent the proximal end of tubular body member 14 are a pair of handles 18, 20. Handle 20 is movable toward and away from handle 18 to manipulate tool 12 as described hereafter. Stationary handle 18 includes a body section 22 extending therefrom, to which elongated tubular body member 14 is secured.

Handle 20 is pivotally connected to stationary handle 18 by suitable means such as a pivot pin 26 so that handle 20 is movable toward and away from handle 18 to manipulate tool 12 between a first retracted position, as shown in FIG. 2, and a second deployed position, as shown in FIG. 3. In order that handle 20 may be incrementally moved toward and away from handle 18, and retained in an intermediate position, a pair of arcuate ratcheting arms 28 may be included, which overlap and extend between handles 18, 20 to retain handles 18, 20 in intermediate positions.

An elongated flexible member 32 is positioned within body member 14 and is attached within body section 22. Flexible member 32 is formed of a suitable material such as nylon or spring steel which may be wound while providing a suitable rigidity to longitudinally travel within body member 14 to manipulate endoscopic tool 12. Flexible member 32 may be of single piece construction or may be joined to a more rigid rod member 33 through coupling member 35 as shown in FIG. 2. Flexible member 32 is peripherally wound around a rotatable flywheel spool member 34, which is rotatively connected to body section 22 by suitable means such as a shoulder pin 36. One end of flexible member 32 extends longitudinally therefrom into tubular body member 14 to communicate with distal endoscopic tool 12 for manipulating tool 12. Flywheel spool member 34 may be spring biased to automatically return the spool 34 and flexible member 32 to its original position when ratchet 28 is released.

In order that flexible member 32 may communicate with tool 12 an elongated, longitudinally movable rod 33 may be provided which is positioned coaxially within tubular member 14. Rod 33 has its proximal end connected to flexible member 32 so that movable rod 33 moves longitudinally as flexible member 32 is unwound and rewound. Secured at the distal end of movable rod 33 is tool 12. Alternatively, for example, flexible member 32 may be secured directly to tool 12 to manipulate tool 12 as flexible member 32 is unwound and rewound.

A link member 42 is joined to movable handle 20 by means such as a shoulder pin 44 so that link member 42 is movable by the motion of handle 20 toward and away from handle 18. A slot 46 is provided and extends radially along flywheel 34. A pin 50 passes through slot 46 and is secured to an end of link member 42 as shown. An arcuate slot 48 (shown in phantom FIGS. 2 and 3), formed integrally in the wall of handle body 22 is provided and engages pin 50, to provide a path of travel for pin 50. The movement of link member 42 by the motion of handle 20 toward and away from handle 18 causes pin member 50 to follow an arcuate path provided by arcuate slot 48 while pin member 50 moves radially in slot 46 along flywheel spool 34 to cause spool 34 to rotate and unwind and rewind flexible member 32.

In order that flywheel spool 34 may be rotated such that flexible member 32 is unwound to manipulate tool 12, motion of handle 20 toward handle 18 causes link member 42 to move clockwise from the position shown in FIG. 2. to that shown in FIG. 3. The clockwise movement of link member 42 causes pin member 50 to move similarly and follow an arcuate path defined by arcuate slot 48 while moving at the same time radially within slot 46, thus rotating flywheel spool 34 clockwise to unwind flexible member 42 and deploy tool 12. In order that flywheel spool 34 may be rotated such that flexible member 32 is rewound to return tool 12 from its position in FIG. 3 to its position in FIG. 2, motion of handle 20 away from handle 18 causes link member 42 to move counterclockwise. The movement of link member 42 counterclockwise causes pin 50 to move similarly and follow an arcuate path defined by arcuate slot 48, while pin 50 moves radially within slot 46, thus rotating flywheel spool 34 counterclockwise to rewind flexible member 42.

One embodiment of the instrument provides a laparoscopic retractor device suitable for displacing tissue and organs within the abdominal cavity of the body. In this embodiment, handle 10 carries a distal laparoscopic tool 12 in the form of a plurality of elongated finger members 52 which are retained in a first, retracted position within distal end portion 16 of tubular body member 14, as shown in FIG. 2. As may be appreciated, finger members 52 are movable longitudinally between their retracted position and a second extended position outside distal end portion 16 of tubular body member 14. In their retracted position, the distal finger members 52 and a portion of tubular body member 14 may be inserted through a cannula positioned in a small incision in the abdominal wall. Finger members 52 may fan out to a pattern shown in FIGS. 5a, 5b, 6a and 6b. Finger members 52 are preferably constructed of a spring steel material or other shape memory material.

While the invention has been particularly shown and described with reference to the preferred embodiment, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. An endoscopic or laparoscopic surgical instrument comprising:
    a handle assembly including a housing and at least one movable handle member;
    a body portion extending from said housing of said handle assembly including a tubular member having a lumen and a flexible member, said flexible member slidably positioned within said tubular member and operatively connected to said movable handle, said flexible member terminating in a tool mechanism; and
    rotatable means positioned within said housing of said handle for extending and withdrawing said tool mechanism from within said lumen upon movement of said movable handle member;
    wherein said flexible member is at least partially wound about said rotatable means and extends at least partially through said tubular member.

2. An instrument according to claim 1, further comprising means for linking said rotatable means to said movable handle member.

3. An instrument according to claim 1, wherein said rotatable means comprises a spool member, said flexible member being at least partially wound on said spool member.

4. An instrument according to claim 3, further comprising means for linking said spool member to said movable handle member.

5. An instrument according to claim 4, wherein said linking means is joined to said spool member by a pin, said pin being positioned in a radially directed slot in said spool member.

6. An instrument according to claim 5, wherein said pin is positioned within an arcuate guide slot formed in said housing.

7. An instrument according to claim 1, wherein said tool mechanism comprises a retractor device.

8. An instrument according to claim 7, wherein movement of said handle member in a first direction withdraws said retractor device into said tubular member, and movement of said handle member in a second direction extends said retractor out of said tubular member.

9. An instrument according to claim 1, further comprising a rod member positioned within said tubular member and coupled at a proximal end to said flexible member and at a distal end to said tool mechanism.

10. An endoscopic or laparoscopic surgical instrument comprising:
    a handle assembly including a housing and at least one movable handle member, said housing having a rotatable member positioned therein;
    a body portion extending from said handle assembly including a tubular member having a lumen and an inner rod member positioned within said tubular member, said rod member terminating in a tool member;
    a flexible member joining said rotatable member and said inner rod member, and
    means for translating movement of said movable handle member into rotation of said rotatable member,
    wherein said flexible member is at least partially wound on said rotatable member to effect extension and withdrawal of said tool member from within said lumen with respect to said tubular member upon movement of said movable handle member.

11. An instrument according to claim 10, wherein said translating means comprises a linkage arm secured at one end to said movable handle and at a second end to said rotatable member.

12. An instrument according to claim 11, wherein said linkage arm is secured to said rotatable member by a pivot pin, said pin being positioned in a slot in said rotatable member.

13. An instrument according to claim 12, wherein said pivot pin is engaged in an arcuate slot in said housing, said slot defining a path of travel for said pin.

14. An instrument according to claim 10, wherein said rotatable member comprises a spool member, said flexible member being at least partly wound on said spool member.

15. An instrument according to claim 10, wherein said tool mechanism comprises a retractor device.

16. An endoscopic or laparoscopic retractor device comprising:
    a handle assembly including a housing and at least one movable handle member;
    a body portion secured to said handle assembly including an outer tubular member and a flexible inner rod member positioned within said tubular member;
    a plurality of flexible finger members positioned on said flexible inner rod member at an end opposite said handle assembly; and
    rotatable means having said flexible member at least partially wound thereon for translating movement of said handle member to movement of said flexible inner rod member to deploy and withdraw said plurality of finger members from within said outer tubular member.

17. A retractor according to claim 16, wherein said rotatable means comprises a spool member, said flexible inner rod member being at least partly wound on said spool member.

18. A retractor according to claim 16, further comprising a linkage arm positioned between said movable handle member and said rotatable means for translating movement of said handle member to movement of said inner rod member.

19. A retractor according to claim 18, wherein said linkage arm is joined to said rotatable means at a pivot pin, said pin being positioned in a radially directed slot in said rotatable means.

20. A retractor according to claim 19, wherein said pin extends into an arcuate slot formed in said housing, said arcuate slot defining a path of travel for said pin.

21. A retractor according to claim 16, further comprising a rigid rod member extending between said flexible rod member and said finger members.

* * * * *